United States Patent [19]

Schubart

[11] Patent Number: 5,312,982
[45] Date of Patent: May 17, 1994

[54] PROCESS FOR THE PREPARATION OF β-HALOGENO-TERT.-ALKYL-CARBOXYLIC ACID CHLORIDES

[75] Inventor: Rüdiger Schubart, Gladbach, Fed. Rep. of Germany

[73] Assignee: Bayer Aktiengesellschaft, Leverkusen, Fed. Rep. of Germany

[21] Appl. No.: 862,092

[22] Filed: Apr. 2, 1992

[30] Foreign Application Priority Data

Apr. 12, 1991 [DE] Fed. Rep. of Germany ....... 4111908

[51] Int. Cl.$^5$ ............................................. C07C 51/58
[52] U.S. Cl. .................................................... 562/864
[58] Field of Search ........................................ 562/864

[56] References Cited

FOREIGN PATENT DOCUMENTS 3618928 12/1986 Fed. Rep. of Germany .
1159470 9/1967 United Kingdom .

OTHER PUBLICATIONS

M. S. Kharasch, Journal of the American Chemical Society, (1940), pp. 925–929.
Patent Abstracts of Japan, vol. 4, No. 66, (4 Jun. 1980).
A. Streitwieser and C. H. Heathcock, "Introduction to organic chemistry", (1976), pp. 77–84.

*Primary Examiner*—Paul J. Killos
*Attorney, Agent, or Firm*—Sprung Horn Kramer & Woods

[57] ABSTRACT

The invention relates to a new process for the preparation of known β-halogeno-tert.-alkylcarboxylic acid chlorides of the general formula (I)

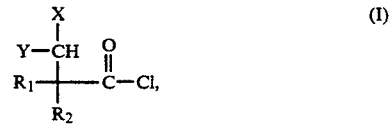

in which
X represents chlorine,
Y represents hydrogen or chlorine,
$R_1$ represents in each case straight-chain or branched lower alkyl or halogeno alkyl and
$R_2$ represents in each case straight-chain or branched lower alkyl or halogeno alkyl or optionally halogen- and/or trifluoromethyl-substituted phenyl, where tert.-alkylcarboxylic acid chlorides of the general formula (II)

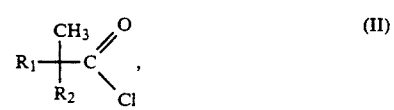

in which
$R^1$ and $R^2$ are defined as above, are reacted with elementary chlorine optionally under irradiation or in the presence of free-radical catalysts.

7 Claims, No Drawings

PROCESS FOR THE PREPARATION OF β-HALOGENO-TERT.-ALKYL-CARBOXYLIC ACID CHLORIDES

The invention relates to a new process for the preparation of known β-halogeno-tert.-alkylcarboxylic acid chlorides, which can be used as intermediates on the one hand for the synthesis of rubber additives and on the other hand as important intermediates for the synthesis of herbicidal active ingredients (cf. U.S. Pat. No. 4 033 904.1).

It is already known that e.g. β-monochloro-tert.-butylcarboxylic acid chloride is obtained by reaction of tert.-butylcarboxylic acid chloride with sulphuryl chloride (J. Amer. Chem. Soc. 62, 925/1940) in the presence of a chlorination catalyst.

Normally the catalysts used are peroxides or azo compounds, or the reaction is carried out under irradiation by UV light, with apparatuses generally used for reactions catalysed by UV light.

The poor yields of the desired monochlorotert.-butylcarboxylic acid chloride are a disadvantage of this synthesis. Further, the gas-phase chlorination of the tert.-butylcarboxylic acid chloride has also been disclosed [DE-OS (German Published Specification) 3 618 928 A1 (1986)].

However, this process has the considerable disadvantage that the chlorination can only be carried out extremely slowly, as an excess of chlorine must always be avoided. This excess leads to the preferential formation of by-products, so that large quantities of product per unit time cannot be prepared by this preparation variant. The important factor of the space-time yield is very unfavourable in this case.

With the present invention, a process is presented that permits β-halogen -tert.-alkylcarboxylic acid chlorides of the formula (I)

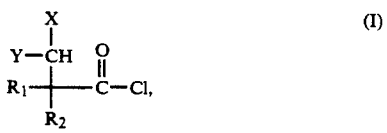

in which
X represents chlorine,
Y represents hydrogen or chlorine,
$R_1$ represents in each case straight-chain or branched lower alkyl or halogeno alkyl and
$R_2$ represents in each case straight-chain or branched lower alkyl or halogeno alkyl or represents optionally halogen- and/or trifluoromethyl-substituted phenyl,
to be synthesised in high selectivity and yield, with simultaneously optimal space-time yield, when tert.-alkylcarboxylic acid chlorides of the formula (II)

in which
$R^1$ and $R^2$ have the definition given above, are reacted with elemental chlorine, optionally under irradiation or in the presence of free-radical catalysts, in a suitable apparatus (see in this context for example DE 2 716 896).

It is extremely surprising that the reaction gives high yields with high selectivity and simultaneously optimal space-time yield. From the above-described prior art, a series of by-products was rather to be expected, with at the same time a substantially smaller amount of product per unit time, i.e. a very much more unfavourable space-time yield.

With the aid of the process according to the invention, compounds of the formula (I) are preferably obtained in which $R_1$ and $R_2$ represent lower alkyl such as methyl or ethyl.

Very especially preferably, the compounds of the formula (I) in which X represents chlorine and Y represents hydrogen, i.e. β-monochlorinated tert.-alkylcarboxylic acid chlorides, may be synthesised by the process according to the invention.

The process according to the invention, with the use of tert.-butylcarboxylic acid chloride, can be described by the following equation:

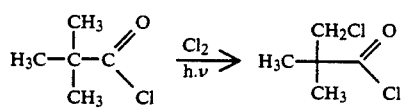

The process according to the invention is preferably carried out in bulk, that is without a diluent. However, it can also be carried out in the presence of suitable inert solvents such as chloroform or tetrachloromethane.

The direct chlorination of the compounds of the formula (II) can if necessary be supported by free-radical catalysts such as peroxides or azo compounds in a conventional manner by continuous addition. However, the use of UV light for the chlorination catalysis is chemically cleaner, it being possible to use conventional UV sources.

The irradiation can be carried out for example using a water-cooled high-pressure mercury vapour lamp, it being possible to use the halogenation lamp either as an immersion lamp, or mounted externally. In mounting the lamp, care must be taken that as much light as possible reaches the halogenation zone. All high-pressure mercury vapour lamps normal for such halogenations may be used for the process according to the invention. Naturally, other lamps suitable for such halogenations may also be used.

The catalysts used are preferably peroxides, such as for example cumyl peroxide or benzoyl peroxide, or azo compounds such as for example azoisobutyronitrile (AIBN).

The reaction temperatures can be varied in a wide range when carrying out the process according to the invention. Generally, temperatures between 40° C. and 120° C., preferably between 60° C. and 110° C., especially preferably between 85° C. and 100° C., are employed. In particular, the temperatures employed are in the region of the boiling point of the tert.-alkylcarboxylic acid chloride to be chlorinated or of the diluent.

The process according to the invention can be carried out at atmospheric pressure or at superatmospheric pressure up to 2000 mbar. Generally, atmospheric pressure is employed.

In a correspondingly suitable apparatus, which for example consists of a distillation flask, a packed column, a condenser and the chlorination device, the starting material is first evaporated. This passes through the column to the condenser, and condenses there.

The condensed starting material can now, either in whole or in part, be passed through the chlorination zone, which is simultaneously irradiated and supplied with chlorine. The reaction mixture that has formed in this chlorination zone, consisting of starting material and product of the formula (I), is now passed to the separation column for separation into the components.

A correspondingly suitable apparatus is for example described in DE 2 716 896. However, in principle other types of apparatus are also usable for this circulatory process.

The process according to the invention can be carried out in two different variants: as a batch chlorination (discontinuous chlorination) (variant 1) or in the form of a continuous halogenation (variant 2).

In variant 1 of the process according to the invention, approximately equimolar quantities of starting material (e.g. tert.-butylcarboxylic acid chloride) and chlorine are continuously, simultaneously and separately introduced into a flooded reaction zone under irradiation or under sustained addition of a usual catalyst, the reaction mixture which forms, containing starting material of the formula (II) and product of the formula (I), simultaneously being removed from the reaction zone.

This mixture is passed to a column for fractionation, and non-halogenated starting material of the formula (II) is immediately separated off and returned to the halogenation zone. This is repeated until almost all of the starting material has been converted.

For carrying out variant 2 of the process (continuous halogenation, when the monohalogenated compounds of the formula (I) are to be obtained, then equivalent amounts, or a slight excess, of halogen are generally used per mole of tert.-alkylcarboxylic acid chloride of the formula (II). When a dihalogenated compound of the formula (I) is to be prepared, then, generally, equivalent amounts or an excess of halogen, preferably up to 2.25 mol, especially preferably up to 2.05 mol, are used per mole of tert.-alkylcarboxylic acid chloride. Preferably, a small excess of halogen is used in the continuous halogenation for preparation of the dihalogenated compounds.

If the process is carried out in the presence of catalysts, then, per mole of tert.-alkylcarboxylic acid chloride of the formula (II), generally 0.001 to 1.5%, preferably 0.02 to 1% and especially preferably 0.1 to 0.5% of catalyst is continuously added.

In the continuous procedure (variant 2), fresh starting material from a stock vessel is added to the separated starting material and returned to the halogenation zone, so that the halogenation can be continued for as long as is desired.

The halogenation reaction of all the tert.-alkylcarboxylic acid chloride used can be carried out to almost complete conversion; as a rule, in the case of the batch procedure (variant 1), chlorination proceeds up to $\geq$ 95%. Then the halogenation reaction is interrupted. Naturally, the reaction could instead be interrupted at an earlier conversion time point, e.g. at about 60% conversion. Conversion is defined in this context as 100% starting material minus the starting material still present. The reaction mixture is then fractionated in order to recover non-halogenated starting material, which is returned to the reaction.

The halogenated tert.-alkylcarboxylic acid chloride, i.e. compounds of the formula (I), is separated off at the bottom of the apparatus, and, if of sufficient purity, is used directly for further reactions, or continuously removed from the apparatus and subjected to fine fractionation.

This gives a continuous process in which reaction mixture is continuously removed and fresh starting material and chlorine are continuously supplied to the circulatory process.

The mixing of the halogen in the flooded reaction zone can be achieved e.g. by stirring, by the flow of the reaction partners during addition in a Venturi tube, or a combination of these possibilities as well as other possible suitable devices.

In this manner mono- or dihalogenated compounds of the formula (I) are obtained as desired in high yield and purity, and the formation of by-products is restricted. With a relatively small apparatus, large amounts of the desired product can be prepared per unit of time by the continuous procedure.

In the batchwise variant 1 and also the continuous reaction procedure (variant 2), the chlorination of the tert.-alkylcarboxylic acid chloride passing through the chlorination zone is generally carried out to a conversion between 0.1 and 30%, preferably between 2 and 20%, especially preferably between 5 and 15%, so that, in total, chlorine and tert.-alkylcarboxylic acid chloride are supplied to the apparatus, and chlorinated tert.-alkylcarboxylic acid chloride practically free from starting material is removed from the apparatus. In both the batch halogenation as well as the continuous halogenation, the reaction can be interrupted and the process resumed after some time. The reaction mixture can also be set aside, and only further processed after some time.

In principle, both reaction variants are also applicable to the bromination of tert.-alkylcarboxylic acid chlorides.

The advantage of this procedure is that the proportion of unusable by-products, and thus the amount of material loss (i.e. loss of starting material of the formula II), is markedly lower.

With this preparation method, the yield of $\beta$-halogenotert.-alkylcarboxylic acid chloride from a defined quantity of tert.-alkylcarboxylic acid chloride per unit of space and time is markedly improved.

The process according to the invention is illustrated by the example below.

A laboratory apparatus suitable for batchwise or continuous chlorination is charged with 689 g (5.7 mol) of tert.-butylcarboxylic acid chloride, which is then slowly chlorinated as described above by partial chlorination of a circulated stream of starting material in a completely flooded reaction zone under UV irradiation ($H_2$ high pressure lamp), where the chlorination temperature is maintained at or only slightly below the boiling point of the tert.-butylcarboxylic acid chloride. When the conversion has reached approximately $\geq$95%, the reaction can be interrupted (variant 1), or tert.-butylcarboxylic acid chloride and chlorine in a ratio of 1:1.06 can be continuously supplied to the apparatus and chlorination zone respectively, and chlorinated product containing virtually no starting material can be removed from the apparatus (variant 2).

689 g ($\sim$5.7 mol) of tert.-butylcarboxylic acid chloride give, at a conversion of $\sim$98%, a crude product which has the following composition (GC, area %):

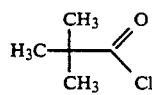

2%

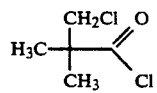

90%

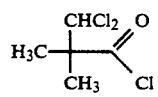

3,2%

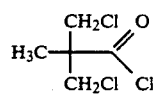

3,5%

Fractionation of the crude product gives 780 g monochloro-tert.-butylcarboxylic acid chloride having a boiling point of 60° C. at 20 mbar and a purity of 98%. This corresponds to a yield of ~90% of theory. 2% of the starting material can be recovered, and are consequently subtracted from the calculation of the yield.

It will be understood that the specification and examples are illustrative but not limitative of the present invention and that other embodiments within the spirit and scope of the invention will suggest themselves to those skilled in the art.

What is claimed is:

1. A process for the preparation of β-halogeno-tert.-alkylcarboxylic acid chlorides of the formula (I)

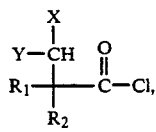

in which
X represents chlorine,
Y represents hydrogen or chlorine,
$R_1$ represents in each case straight-chain or branched lower alkyl or halogeno alkyl and
$R_2$ represents in each case straight-chain or branched lower alkyl or halogeno alkyl or represents optionally halogen- and/or trifluoromethyl-substituted phenyl,
which comprises reacting a tert.-alkylcarboxylic acid chloride of the formula (II)

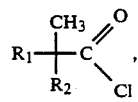

in which
$R^1$ and $R^2$ have the definition given above with elemental chlorine in the liquid phase, optionally under irradiation or in the presence of free-radical catalysts in a suitable apparatus.

2. A process according to claim 1, wherein $R^1$ represents methyl, ethyl, n- or iso-propyl, n-, iso-, sec.-, tert.-butyl and their monohalogenated derivatives, and $R^2$ represents methyl, ethyl, n- or iso-propyl, n-, iso-, sec.- or tert.-butyl and their monohalogenated derivatives or represents optionally mono- to trisubstituted phenyl, identically or differently substituted by fluorine, chlorine, bromine and/or trifluoromethyl.

3. A process according to claim 1, wherein $R^1$ represents methyl or ethyl and $R^2$ represents methyl, ethyl or phenyl.

4. The process according to claim 1, wherein peroxides or azo compounds are used as catalysts.

5. The process according to claim 1, wherein the reaction is carried out as a batch chlorination.

6. The process according to claim 1, wherein the reaction is carried out as a continuous halogenation.

7. The process according to claim 1, wherein the chlorination is carried out to a conversion of between 0.1 and 30% of the tert.-alkylcarboxylic acid chloride passing through the chlorination zone.

* * * * *

UNITED STATES PATENT AND TRADEMARK OFFICE
CERTIFICATE OF CORRECTION

PATENT NO : 5,312,982
DATED : May 17, 1994
INVENTOR(S): Rudiger, Schubart

It is certified that error appears in the above-identified patent and that said Letters Patent is hereby corrected as shown below:

Col. 6, Line 44    After "chlorination" insert --(variant 1)--

Col. 6, Line 46    After "halogenation" insert --(variant 2)--

Signed and Sealed this

Second Day of May, 2000

Attest:

Q. TODD DICKINSON

Attesting Officer    Director of Patents and Trademarks